US012799352B2

(12) United States Patent
Uno et al.

(10) Patent No.: US 12,799,352 B2
(45) Date of Patent: Nov. 17, 2026

(54) COMPOUND, METHOD FOR PRODUCING COMPOUND, AND METHOD FOR PRODUCING SURFACE TREATMENT AGENT

(71) Applicant: AGC Inc., Tokyo (JP)

(72) Inventors: Makoto Uno, Chiyoda-ku (JP); Eiichiro Anraku, Chiyoda-ku (JP); Takafumi Kawakami, Chiyoda-ku (JP); Keigo Matsuura, Chiyoda-ku (JP)

(73) Assignee: AGC Inc., Tokyo (JP)

( * ) Notice: Subject to any disclaimer, the term of this patent is extended or adjusted under 35 U.S.C. 154(b) by 583 days.

(21) Appl. No.: 18/454,254

(22) Filed: Aug. 23, 2023

(65) Prior Publication Data

US 2023/0392039 A1 Dec. 7, 2023

Related U.S. Application Data

(63) Continuation of application No. PCT/JP2022/008825, filed on Mar. 2, 2022.

(30) Foreign Application Priority Data

Mar. 5, 2021 (JP) ................................ 2021-035096

(51) Int. Cl.

| | |
|---|---|
| ***C09D 171/02*** | (2006.01) |
| ***C07C 17/35*** | (2006.01) |
| ***C07C 22/08*** | (2006.01) |
| ***C08G 65/22*** | (2006.01) |
| ***C08G 65/337*** | (2006.01) |
| ***C09D 5/00*** | (2006.01) |

(52) U.S. Cl.

CPC ............ *C09D 171/02* (2013.01); *C07C 17/35* (2013.01); *C07C 22/08* (2013.01); *C08G 65/226* (2013.01); *C08G 65/337* (2013.01); *C09D 5/00* (2013.01)

(58) Field of Classification Search

None

See application file for complete search history.

(56) References Cited

U.S. PATENT DOCUMENTS

2014/0302332 A1 10/2014 Murotani et al.

FOREIGN PATENT DOCUMENTS

| | | | |
|---|---|---|---|
| CN | 108440593 | A | 8/2018 |
| CN | 112334450 | A | 2/2021 |
| JP | 2017-95363 | A | 6/2017 |
| JP | 2018-43940 | A | 3/2018 |
| WO | WO 2013/121984 | A1 | 8/2013 |
| WO | WO-2018/189157 | A1 | 10/2018 |
| WO | WO-2019/049753 | A1 | 3/2019 |
| WO | WO 2019/208503 | A1 | 10/2019 |

OTHER PUBLICATIONS

International Search Report issued May 10, 2022 in PCT/JP2022/008825 filed Mar. 2, 2022 3 pages.

Smilovic, I. G. et al. "Iridium-Catalyzed Chemoselective and Enantioselective Hydrogenation of (I-Chloro-1-Alkenyl) Boronic Esters" Angewandte Chemie International Edition. Jan. 23, 2012, vol. 51, No. 4, pp. 1014-1018 (5 pages).

Braun, T. et al. "C—F Activation at Rhodium Boryl Complexes: Formation of 2-Fluoroalkyl-1,3,2-Dioxaborolanes by Catalytic Functionalization of Hexafluoropropene" Angewandte Chemie. Feb. 23, 2009, vol. 121, No. 10, pp. 1850-1854 (5 pages).

Bismuto, A. et al. "Aluminum-Catalyzed Hydroboration of Alkenes" ACS Catalysis. Jan. 29, 2018, vol. 8, No. 3, pp. 2001-2005 (5 pages).

Jaladi, A. K. et al. "Alkene hydroboration with pinacolborane catalysed by lithium diisobutyl-tertbutoxyaluminum hydride" RSC Advances. Aug. 23, 2019, vol. 9, No. 45, pp. 26483-26486 (4 pages).

Wang, Z. C. et al. "Base-catalysed reductive relay hydroboration of allylic alcohols with pinacolborane to form alkylboronic esters" Chemical Communications. May 30, 2019, vol. 55, No. 60, pp. 8848-8851 (4 pages).

Levin, V. V. et al. "Nucleophilic fluoroalkylation of (bromomethyl)pinacolborane using silicon reagents" Journal of Fluorine Chemistry. Jun. 26, 2013, vol. 154, pp. 43-46 (4 pages).

Pereira, S. et al. "A study of hydroboration of alkenes and alkenes with pinacolborane catalyzed by transition metals" Tetrahedron Letters. May 6, 1996, vol. 37, No. 19, pp. 3283-3286 (4 pages).

Zhang, L. et al. "A Cobalt-Catalyzed Alkene Hydroboration with Pinacolborane" Angewandte Chemie International Edition. Feb. 3, 2014, vol. 53, No. 10, pp. 2696-2700 (5 pages).

Matteson, D.S. "Boronic Esters in Stereodirected Synthesis" Tetrahedron, 1989, vol. 45, No. 7, pp. 1859-1885 (27 pages).

Zhang et al., "Photoinduced Radical Borylation of Alkyl Bromides Catalyzed by 4-Phenylpyridine", Angew. Chem. Int. Ed. vol. 59, 2020, pp. 2095-2099.

*Primary Examiner* — Randy P Gulakowski
*Assistant Examiner* — Holley Grace Hester
(74) *Attorney, Agent, or Firm* — Oblon, McClelland, Maier & Neustadt, L.L.P.

(57) ABSTRACT

There are provided a novel compound, a method for producing the same, and a method for producing a surface treatment agent using the novel compound as a raw material. A compound represented by the following formula (A1) or (A2).

$$G^1\text{-}(CH_2)_n\text{-}M \quad \text{Formula (A1)}$$

$$M\text{-}(CH_2)_n\text{-}G^2\text{-}(CH_2)_n\text{-}M \quad \text{Formula (A2)}$$

where, each reference sign in the formula is as described in the specification.

10 Claims, No Drawings

COMPOUND, METHOD FOR PRODUCING COMPOUND, AND METHOD FOR PRODUCING SURFACE TREATMENT AGENT

INCORPORATION BY REFERENCE

This application is based upon and claims the benefit of priority from Japanese Patent Application 2021-35096 filed on Mar. 5, 2021, and PCT application No. PCT/JP2022/008825 filed on Mar. 2, 2022, the disclosure of which is incorporated herein in its entirety by reference.

BACKGROUND

The present invention relates to a compound, a method for producing a compound, and a method for producing a surface treatment agent.

Fluorine-containing compounds are used in various fields such as agricultural chemicals, pharmaceuticals, and functional materials. It is required to synthesize various structures by a simpler method. For example, in order to impart various functions to a compound having a fluoroalkyl group or a (poly)oxyfluoroalkylene chain, synthesis methods for introducing various substituents have been studied.

Various studies have been made on a method for synthesizing a compound having a structure in which an alkyl group is bonded to a fluoroalkyl group.

For example, Japanese Unexamined Patent Application Publication No. 2018-43940 discloses a method for producing a fluorine-containing compound by adding a perfluoroalkyl bromide to an olefin compound by a radical reaction.

SUMMARY

The technique of Japanese Unexamined Patent Application Publication No. 2018-43940 is not suitable for synthesis of a compound having a carbon-carbon double bond because an olefin is reacted, and the type of electrophile is limited. In addition, since the product can further undergo a radical reaction to be telomerized, there is a problem that various types of by-products are generated.

An object of the present invention is to provide a novel compound, a method for producing the same, a method for producing another compound using the novel compound as a raw material, and a method for producing a surface treatment agent.

The present invention provides a compound, a method for producing the same, and a method for producing a surface treatment agent having the following configurations [1] to [4].

$G^1$-$(CH_2)_n$-M   Formula (A1)

M-$(CH_2)_n$-$G^2$-$(CH_2)_n$-M   Formula (A2)

where, in the formula, $G^1$ is a fluoroalkyl group or a monovalent group having a (poly)oxyfluoroalkylene chain, $G^2$ is a fluoroalkylene group or a divalent group having a (poly)oxyfluoroalkylene chain, M is $BR^1R^2$, $R^1$ and $R^2$ are each independently a group represented by —OH, —$R^5$, —$OR^5$, —O—C(O)—$R^5$, or —$NR^5R^6$, $R^5$ is a hydrocarbon group which may have a substituent or a heteroatom in a carbon chain, two $R^5$'s may be linked to form a ring structure, $R^6$ is a hydrogen atom or an alkyl group having 1 to 6 carbon atoms, and when there are a plurality of M's, the M's may be the same as or different from each other, and n is an integer of 2 to 20.

[2] A method for producing the compound according to [1], the method including: reacting a compound represented by the following formula (B1) or (B2) and a compound represented by the following formula (C1).

$G^1$-$(CH_2)_{n-2}$—CH═$CH_2$   Formula (B1)

$CH_2$═CH—$(CH_2)_{n-2}$-$G^2$-$(CH_2)_{n-2}$—CH═$CH_2$   Formula (B2)

$HBR^1R^2$   Formula (C1)

where, in the formula, $G^1$ is a monovalent group having a (poly)oxyfluoroalkylene chain, $G^2$ is a divalent group having a (poly)oxyfluoroalkylene chain, $R^1$ and $R^2$ are each independently a group represented by —OH, —$R^5$, —$OR^5$, —O—C(O)—$R^5$, or —$NR^5R^6$, $R^5$ is a hydrocarbon group which may have a substituent or a heteroatom in a carbon chain, two $R^5$'s may be linked to form a ring structure, and $R^6$ is a hydrogen atom or an alkyl group having 1 to 6 carbon atoms, and n is an integer of 2 to 20.

[3] A method for producing a compound represented by the following formula (E1) or (E2), the method including: reacting the compound according to [1] with a compound represented by the following formula (D).

$R^{11}$—$X^1$   Formula (D)

$G^1$-$(CH_2)_n$—$R^{11}$   Formula (E1)

$R^{11}$—$(CH_2)_n$-$G^2$-$(CH_2)_n$—$R^{11}$   Formula (E2)

where, in the formula, $G^1$ is a fluoroalkyl group or a monovalent group having a (poly)oxyfluoroalkylene chain, $G^2$ is a fluoroalkylene group or a divalent group having a (poly)oxyfluoroalkylene chain, n is an integer of 2 to 20, $R^{11}$ is a hydrocarbon group which may have a substituent or a heteroatom, and $X^1$ is a halogen atom.

[4] A method for producing a surface treatment agent, the method including: obtaining a compound represented by the formula (E1) or (E2) by the production method according to [3]; and introducing a reactive silyl group into the compound.

The above and other objects, features and advantages of the present disclosure will become more fully understood from the detailed description given hereinbelow which are given by way of illustration only, and thus are not to be considered as limiting the present disclosure.

The present invention provides a novel compound, a method for producing the same, a method for producing another compound using the novel compound as a raw material, and a method for producing a surface treatment agent.

DESCRIPTION OF EMBODIMENTS

In the present specification, the compound represented by the formula (A1) is referred to as a compound (A1). The same applies to compounds represented by other formulae and the like.

The "(poly)oxyfluoroalkylene" is a generic term for oxyfluoroalkylene and polyoxyfluoroalkylene.

The fluoroalkyl group is a generic term for a combination of a perfluoroalkyl group and a partial fluoroalkyl group.

The perfluoroalkyl group means a group in which all hydrogen atoms of the alkyl group are substituted with fluorine atoms. In addition, the partial fluoroalkyl group is an alkyl group in which one or more hydrogen atoms are substituted with a fluorine atom and which has one or more hydrogen atoms.

That is, the fluoroalkyl group is an alkyl group having one or more fluorine atoms.

The "reactive silyl group" is a generic term for a hydrolyzable silyl group and a silanol group (Si—OH), and the "hydrolyzable silyl group" means a group capable of forming a silanol group by a hydrolysis reaction.

The "surface layer" means a layer formed on the surface of the substrate.

"to" indicating a numerical range means that the numerical values stated before and after "to" are included as a lower limit value and an upper limit value.

[Compound (A1) and compound (A2)]

The compound according to the present invention (hereinafter also referred to as the present compound) is a compound represented by the following formula (A1) or (A2).

$G^1$-$(CH_2)_n$-M    Formula (A1)

M-$(CH_2)_n$-$G^2$-$(CH_2)_n$-M    Formula (A2)

where, in the formula, $G^1$ is a fluoroalkyl group or a monovalent group having a (poly)oxyfluoroalkylene chain, $G^2$ is a fluoroalkylene group or a divalent group having a (poly)oxyfluoroalkylene chain, M is $BR^1R^2$, $R^1$ and $R^2$ are each independently a group represented by —OH, —$R^5$, —$OR^5$, —O—C(O)—$R^5$, or —$NR^5R^6$, $R^5$ is a hydrocarbon group which may have a substituent or a heteroatom in a carbon chain, two $R^5$'s may be linked to form a ring structure, $R^6$ is a hydrogen atom or an alkyl group having 1 to 6 carbon atoms, and when there are a plurality of M's, the M's may be the same as or different from each other, and n is an integer of 2 to 20.

The present compound has a structure in which a fluoroalkyl chain or a (poly)oxyfluoroalkylene chain and an alkyl chain are linked by a carbon-carbon bond or an oxygen-carbon bond without any bond such as an ester bond and an amide bond, and the alkyl chain has a boron-based substituent (M).

As described above, the present compound is excellent in chemical stability because a fluoroalkyl chain or a (poly)oxyfluoroalkylene chain and an alkyl chain are linked without any bond. In addition, in the present compound, the alkyl chain has the substituent M. The present compound having such a structure is a preferred compound as a raw material for obtaining a fluoroalkyl chain or a (poly)oxyfluoroalkylene chain to which a substituent is easily introduced at the M position and various functionalities are imparted by a one-step or multi-step reaction.

The fluoroalkyl group in $G^1$ may be a linear fluoroalkyl group or a fluoroalkyl group having a branched or ring structure. The number of carbon atoms in the fluoroalkyl group may be appropriately adjusted according to the application of the present compound. From the viewpoint of ease of production of the present compound and an increase in yield in the production of other compounds using the present compound as a raw material, the number of carbon atoms is preferably 1 to 30, more preferably 1 to 20, still more preferably 1 to 10, and particularly preferably 1 to 6.

Specific examples of the fluoroalkyl group include $CF_3$—, $CHF_2$—, $CF_3CF_2$—, $CF_3CHF$—, $CF_3CF_2CF_2$—, $CF_3CHFCF_2$—, $CF_3CHFCHF$—, $CF_3CF(CF_3)$—, $CF_3CF_2CF_2CF_2$—, $CF_3CHFCF_2CF_2$—, $CF_3CF(CF_3)$—$CF_2$—, $CF_3C(CF_3)_2$—$CF_2$—, $CF_3CF_2CF_2CF_2CF_2$—, $CF_3CF_2CF_2CF_2CF_2CF_2$—, a fluorocyclobutyl group, a fluorocyclopentyl group, and a fluorocyclohexyl group.

The monovalent group having a (poly)oxyfluoroalkylene chain in $G^1$ is a fluoroalkyl group having —O— at a terminal bonded to $CH_2$, —O— between carbon-carbon atoms of a carbon chain having 2 or more carbon atoms, or both of them in the formula (A1). From the viewpoint of ease of production and the like, $G^1$ preferably has a structure represented by the following formula (G1-1).

$R^{f0}O$—$[(R^{f1}O)_{m1}(R^{f2}O)_{m2}(R^{f3}O)_{m3}(R^{f4}O)_{m4}(R^{f5}O)_{m5}(R^{f6}O)_{m6}]$—$(R^{f7})_{m7}$—    Formula (G1-1)

where $R^{f0}$ is a fluoroalkyl group having 1 to 20 carbon atoms, $R^{f1}$ is a fluoroalkylene group having 1 carbon atom, $R^{f2}$ is a fluoroalkylene group having 2 carbon atoms, $R^{f3}$ is a fluoroalkylene group having 3 carbon atoms, $R^{f4}$ is a fluoroalkylene group having 4 carbon atoms, $R^{f5}$ is a fluoroalkylene group having 5 carbon atoms, $R^{f6}$ is a fluoroalkylene group having 6 carbon atoms, $R^{f7}$ is a fluoroalkylene group having 1 to 6 carbon atoms, m1, m2, m3, m4, m5, and m6 each independently represent an integer of 0 or 1 or more, m7 is an integer of 0 or 1, and m1+m2+m3+m4+m5+m6+m7 is an integer of 0 to 200.

Note that the bonding order of $(R^{f1}O)$ to $(R^{f6}O)$ in the formula (G1-1) is random.

m1 to m6 in the formula (G1-1) represent the number of $(R^{f1}O)$ to $(R^{f6}O)$, respectively, and do not represent arrangement. For example, $(R^{f5}O)_{m5}$ represents that the number of $(R^{f5}O)$ is m5, and does not represent a block arrangement structure of $(R^{f5}O)_{m5}$. Similarly, the order of description of $(R^{f1}O)$ to $(R^{f6}O)$ does not represent the bonding order of the respective units.

When m7 is 0, the terminal of $G^1$ bonded to $CH_2$ is —O—. When m7 is 1, the terminal of $G^1$ bonded to $CH_2$ is a carbon atom (carbon atom at the terminal of $R^{f7}$).

The fluoroalkylene group having 3 to 6 carbon atoms may be a linear fluoroalkylene group or a fluoroalkylene group having a branched or ring structure.

For example, when the compound (A1) is used as a raw material of a surface treatment agent, m1+m2+m3+m4+m5+m6 is an integer of 1 to 200, that is, $G^1$ is preferably a polyoxyfluoroalkylene chain from the viewpoint of water/oil repellency, fingerprint removability, and the like.

In addition, for example, m7 is preferably 1 from the viewpoint of chemical stability of the compound (A1).

Specific examples of $R^{f1}$ include —$CF_2$— and —CHF—.

Specific examples of $R^{f2}$ include —$CF_2CF_2$—, —$CHFCF_2$—, —CHFCHF—, —$CH_2CF_2$—, and —$CH_2CHF$—.

Specific examples of $R^{f3}$ include —$CF_2CF_2CF_2$—, —$CF_2CHFCF_2$—, —$CF_2CH_2CF_2$—, —$CHFCF_2CF_2$—, —$CHFCHFCF_2$—, —CHFCHFCHF—, —$CHFCH_2CF_2$—, —$CHFCH_2CF_2$—, —$CH_2CF_2CF_2$—, —$CH_2CHFCF_2$—, —$CH_2CH_2CF_2$—, —$CH_2CF_2CHF$—, —$CH_2CHFCHF$—, —$CH_2CH_2CHF$—, —$CF(CF_3)$—$CF_2$—, —$CF(CHF_2)$—$CF_2$—, —$CF(CH_2F)$—$CF_2$—, —$CF(CH_3)$—$CF_2$—, —$CF(CF_3)$—CHF—, —$CF(CHF_2)$—CHF—, —$CF(CH_2F)$—CHF—, —$CF(CH_3)$—CHF—, —$CF(CF_3)$—$CH_2$—, —$CF(CHF_2)$—$CH_2$—, —$CF(CH_2F)$—$CH_2$—, —$CF(CH_3)$—$CH_2$—, —$CH(CF_3)$—$CF_2$—, —$CH(CHF_2)$—$CF_2$—, —CH $(CH_2F)—CF_2—$, $—CH(CH_3)—CF_2—$, $—CH(CF_3)—CHF—$, $—CH(CHF_2)—CHF—$, $—CH(CH_2F)—CHF—$, $—CH(CH_3)—CHF—$, $—CH(CF_3)—CH_2—$, $—CH(CHF_2)—CH_2—$, and $—CH(CH_2F)—CH_2—$.

Specific examples of $R^{f4}$ include $—CF_2CF_2CF_2CF_2—$, $—CHFCF_2CF_2CF_2—$, $—CH_2CF_2CF_2CF_2—$, $—CF_2CHFCF_2CF_2—$, $—CHFCHFCF_2CF_2—$, $—CH_2CHFCF_2CF_2—$, $—CF_2CH_2CF_2CF_2—$, $—CHFCH_2CF_2CF_2—$, $—CH_2CH_2CF_2CF_2—$, $—CHFCF_2CHFCF_2—$, $—CH_2CF_2CHFCF_2—$, $—CF_2CHFCHFCF_2—$, $—CHFCHFCHFCF_2—$, $—CH_2CHFCHFCF_2—$, $—CF_2CH_2CHFCF_2—$, $—CHFCH_2CHFCF_2—$, $—CH_2CH_2CHFCF_2—$, $—CF_2CH_2CH_2CF_2—$, $—CHFCH_2CH_2CF_2—$, $—CH_2CH_2CH_2CF_2—$, $—CHFCH_2CH_2CHF—$, $—CH_2CH_2CH_2CHF—$, and $\text{-cyclo}C_4F_6—$.

Specific examples of $R^{f5}$ include $—CF_2CF_2CF_2CF_2CF_2—$, $—CHFCF_2CF_2CF_2CF_2—$, $—CH_2CHFCF_2CF_2CF_2—$, $—CF_2CHFCF_2CF_2CF_2—$, $—CHFCHFCF_2CF_2CF_2—$, $—CH_2CHFCF_2CF_2CF_2—$, $—CF_2CH_2CF_2CF_2CF_2—$, $—CHFCH_2CF_2CF_2CF_2—$, $—CH_2CH_2CF_2CF_2CF_2—$, $—CF_2CF_2CHFCF_2CF_2—$, $—CHFCF_2CHFCF_2CF_2—$, $—CH_2CF_2CHFCF_2CF_2—$, $—CF_2CF_2CHFCF_2CF_2—$, $—CHFCF_2CHFCF_2CF_2—$, $—CH_2CF_2CHFCF_2CF_2—$, $—CH_2CF_2CF_2CF_2CH_2—$, and $\text{-cyclo}C_5F_8—$.

Specific examples of $R^{f6}$ include $—CF_2CF_2CF_2CF_2CF_2CF_2—$, $—CF_2CF_2CHFCHFCF_2CF_2—$, $—CHFCF_2CF_2CF_2CF_2CF_2—$, $—CHFCHFCHFCHFCHFCHF—$, $—CHFCF_2CF_2CF_2CF_2CH_2—$, $—CH_2CF_2CF_2CF_2CF_2CH_2—$, and $\text{-cyclo}C_6F_{10}—$.

In addition, specific examples of $R^{f0}$ and $R^{f7}$ include the same ones as those mentioned in the above $R^{f1}$ to $R^{f6}$.

Here, $\text{-cyclo}C_4F_6—$ means a perfluorocyclobutanediyl group, and specific examples thereof include a perfluorocyclobutane-1,2-diyl group. $\text{-cyclo}C_5F_8—$ means a perfluorocyclopentanediyl group, and specific examples thereof include a perfluorocyclopentane-1,3-diyl group. $\text{-cyclo}C_6F_{10}—$ means a perfluorocyclohexanediyl group, and specific examples thereof include a perfluorocyclohexane-1,4-diyl group.

When the compound (A1) is used as a raw material of a surface treatment agent, G1 is preferably a monovalent group having a (poly)oxyfluoroalkylene chain, and more preferably a monovalent group having a polyoxyfluoroalkylene chain, from the viewpoint of further excellent water/oil repellency, friction resistance, and fingerprint dirt removability. Among them, it is preferable to have structures represented by the following formulae (F1) to (F3).

$$(R^{f1}O)_{m1}—(R^{f2}O)_{m2}—(R^{f7})_{m7} \quad \text{Formula (F1)}$$

$$(R^{f2}O)_{m2}—(R^{f40})_{m4}—(R^{f7})_{m7} \quad \text{Formula (F2)}$$

$$(R^{f3}O)_{m3}—(R^{f7})_{m7} \quad \text{Formula (F3}$$

where, each reference sign of the formulae (F1) to (F3) is the same as those in the formula (G1-1).

In the above formulae (F1) and (F2), the bonding order of $(R^{f1}O)$ and $(R^{f2}O)$, and $(R^{f2}O)$ and $(R^{f4}O)$ is random. For example, $(R^{f1}O)$ and $(R^{f2}O)$ may be alternately arranged, $(R^{f1}O)$ and $(R^{f2}O)$ may be each arranged in a block, or may be random. The same applies to the formula (F3).

In the formula (F1), m1 is preferably 1 to 30, and more preferably 1 to 20. In addition, m2 is preferably 1 to 30, and more preferably 1 to 20.

In the formula (F2), m2 is preferably 1 to 30, and more preferably 1 to 20. In addition, m4 is preferably 1 to 30, and more preferably 1 to 20.

In the formula (F3), m3 is preferably 1 to 30, and more preferably 1 to 20.

The fluoroalkylene group in $G^2$ may be linear, or may have a branched or ring structure. The number of carbon atoms in the fluoroalkylene group is preferably 1 to 30, more preferably 1 to 20, still more preferably 1 to 10, and particularly preferably 1 to 6 from the viewpoint of increasing the yield of the present production method.

Specific examples of the fluoroalkylene group include the same groups as those mentioned in the above $R^{f1}$ to $R^{f6}$.

The divalent group having a (poly)oxyfluoroalkylene chain in $G^2$ is a fluoroalkylene group having —O— at two terminals bonded to $CH_2$ each independently, or —O— between carbon-carbon atoms of a carbon chain having 2 or more carbon atoms, or is a combination thereof in the formula (A2). From the viewpoint of ease of production and the like, $G^2$ preferably has a structure represented by the following formula (G2-1).

$$—(O)_{m0}—[(R^{f1}O)_{m1}(R^{f2}O)_{m2}(R^{f3}O)_{m3}(R^{f4}O)_{m4}(R^{f5}O)_{m5}(R^{f6}O)_{m6}]—(R^{f7})_{m7}— \quad \text{Formula (G2-1)}$$

Here, m0 is an integer of 0 or 1, and $R^{f1}$, $R^{f2}$, $R^{f3}$, $R^{f4}$, $R^{f5}$, $R^{f6}$, $R^{f7}$, m1, m2, m3, m4, m5, m6, and m7 are the same as those in the $G^1$. Note that the bonding order of $(R^{f1}O)$ to $(R^{f6}O)$ in the formula (G2-1) is random and is as described in the above formula (G1-1).

When m7 is 0, one terminal of G2 bonded to $CH_2$ is —O—. When m7 is 1, one terminal of $G^2$ bonded to $CH_2$ is a carbon atom (carbon atom at the terminal of $R^{f7}$). In addition, when m0 is 1, one terminal of $G^2$ bonded to $CH_2$ is —O—. When m0 is 0, one terminal of $G^2$ bonded to $CH_2$ is a carbon atom (carbon atom at any terminal of $R^{f1}$ to $R^{f7}$). Note that m0 and m7 are each independently 0 or 1.

For example, when the compound (A2) is used as a raw material of a surface treatment agent, m0+m1+m2+m3+m4+m5+m6 is an integer of 2 to 200, that is, $G^2$ is preferably a polyoxyfluoroalkylene chain from the viewpoint of water/oil repellency, fingerprint removability, and the like.

In addition, for example, from the viewpoint of chemical stability of the compound (A2), it is preferable that m0 be 0 or m7 be 1, and it is more preferable that m0 be 0 and m7 be 1.

When the obtained compound (A2) is used as a surface treatment agent or a raw material thereof, $G^2$ preferably has a structure represented by the following formulae (F4) to (F6) from the viewpoint of further excellent water/oil repellency, friction resistance, and fingerprint dirt removability.

$$—(O)_{m0}—(R^{f1}O)_{m1}—(R^{f2}O)_{m2}—(R^{f7})_{m7} \quad \text{Formula (F4)}$$

$$—(O)_{m0}—(R^{f2}O)_{m2}—(R^{f4}O)_{m4}—(R^{f7})_{m7} \quad \text{Formula (F5)}$$

$$—(O)_{m0}—(R^{f3}O)_{m3}—(R^{f7})_{m7} \quad \text{Formula (F6)}$$

where, each reference sign of the formulae (F4) to (F6) is the same as those in the formula (G2-1).

In the above formulae (F4) and (F5), the bonding order of $(R^{f1}O)$ and $(R^{f2}O)$, and $(R^{f2}O)$ and $(R^{f4}O)$ is random. For example, $(R^{f1}O)$ and $(R^{f2}O)$ may be alternately arranged, $(R^{f1}O)$ and $(R^{f2}O)$ may be each arranged in a block, or may be random.

In the formula (F4), m1 is preferably 1 to 30, and more preferably 1 to 20. In addition, m2 is preferably 1 to 30, and more preferably 1 to 20.

In the formula (F5), m2 is preferably 1 to 30, more preferably 1 to 20. In addition, m4 is preferably 1 to 30, and more preferably 1 to 20.

In the formula (F6), m3 is preferably 1 to 30, and more preferably 1 to 20.

The ratio of fluorine atoms in the fluoroalkyl chain and the (poly)oxyfluoroalkylene chain [{number of fluorine atoms/(number of fluorine atoms+number of hydrogen atoms)}×100(%)] in $G^1$ and $G^2$ is preferably 40% or more, more preferably 50% or more, and still more preferably 60% or more from the viewpoint of excellent water/oil repellency and fingerprint removability.

In addition, the molecular weight of the (poly)oxyfluoroalkylene chain part is preferably 200 to 30,000, more preferably 600 to 25,000, still more preferably 800 to 20,000, and particularly preferably 1,000 to 8,000 from the viewpoint of wear resistance.

M represents a boron-based substituent $BR^1R^2$, $R^1$ and $R^2$ are each independently a group represented by —OH, —$R^5$, —$OR^5$, —O—C(O)—$R^5$, or —$NR^5R^6$, $R^5$ is a hydrocarbon group which may have a substituent or a heteroatom in the carbon chain, two $R^5$'s may be linked to form a ring structure, and $R^6$ is a hydrogen atom or an alkyl group having 1 to 6 carbon atoms.

Examples of the hydrocarbon group in $R^5$ include an aliphatic hydrocarbon group (linear alkyl group, branched alkyl group, cycloalkyl group, and the like). The aliphatic hydrocarbon group may have a double bond or a triple bond in the carbon chain. Examples of the substituent that the hydrocarbon group may have include a halogen atom, a hydroxy group, an amino group, a nitro group, a sulfo group, and an oxo group, from the viewpoint of the stability of the compound in the present production method, a halogen atom is preferable. Examples of the halogen atom include a fluorine atom, a chlorine atom, and a bromine atom.

Heteroatoms may be included in the carbon chain alone or in combination with other substituents such as an oxo group. Specific examples of the partial structure containing a heteroatom include —C(O)$NR^{25}$—, —C(O)O—, —C(O)—, —O—, —$NR^{25}$—, —S—, —OC(O)O—, —NHC(O)O—, —NHC(O)$NR^{25}$—, —$SO_2NR^{25}$—, —$Si(R^{25})_2$—, and —$OSi(R^{25})_2$—. Here, $R^{25}$ is a hydrogen atom, an alkyl group having 1 to 6 carbon atoms, or a phenyl group.

Examples of the structure in which two $R^5$'s are linked to form a ring structure include *—$R^5$—*, *—O—$R^5$—*, *—O—$R^5$—O—*, *—O—C(O)—$R^5$—C(O)—O—*, and *—$NR^6$—$R^5$—$NR^6$—*. Here, * is a linking group bonded to B, and a ring structure containing B is formed.

Specific examples of $BR^1R^2$ include the following.

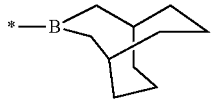
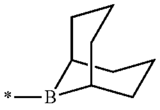
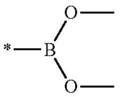
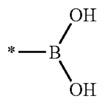
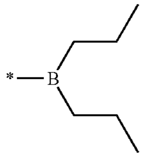
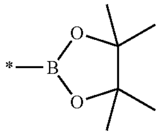
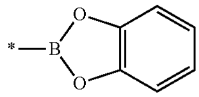
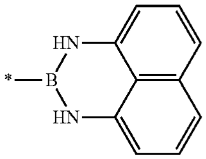
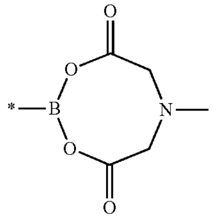

Specific examples of the compound (A1) and the compound (A2) include the following compounds.

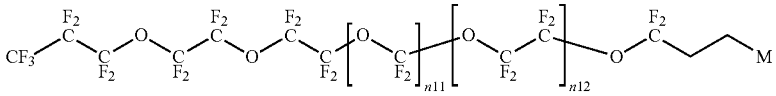
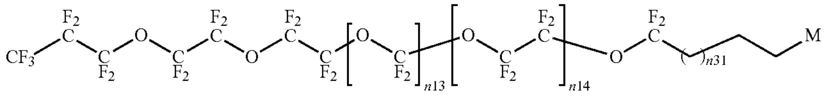
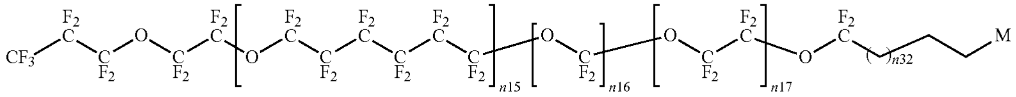
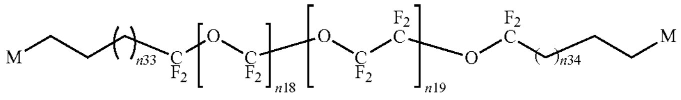
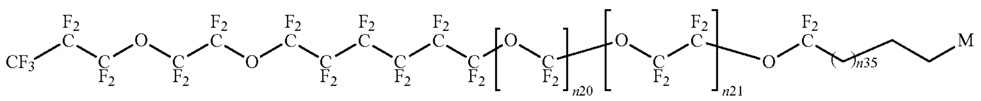
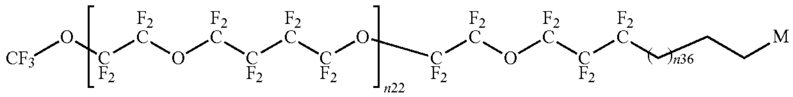

-continued

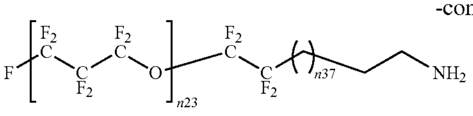
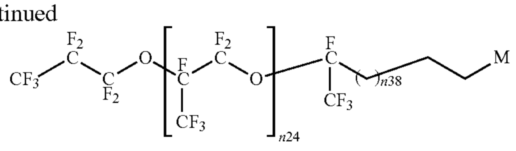

where M is as described above, n11 to n24 represent the number of repeating units and are each independently an integer of 1 to 200, n31 is an integer of 1 to 18, and n32 to n38 are each independently an integer of 0 to 18.

[Method for Producing Compound (A1) or Compound (A2)]

The method for producing the present compound is not particularly limited, but the following production method is preferable from the viewpoint of relatively easy availability of raw materials and excellent yield.

That is, the method for producing the compound (A1) or the compound (A2) according to the present invention includes reacting a compound represented by the following formula (B1) or (B2) with a compound represented by the following formula (C1).

$G^1$-$(CH_2)_{n-2}$—CH═$CH_2$ Formula (B1)

$CH_2$═CH—$(CH_2)_{n-2}$-$G^2$-$(CH_2)_{n-2}$—CH═$CH_2$ Formula (B2)

$HBR^1R^2$ Formula (C1)

where, in the formula, $G^1$, $G^2$, $R^1$, $R^2$, and n are the same as those in the formula (A1) or (A2), and preferred embodiments are also the same.

For example, the compound (B1) or the compound (B2), the compound (C1), and as necessary, a radical polymerization initiator such as an azo-based polymerization initiator are added to a solvent and heated, and accordingly, the compound (C1) is added to the olefin of the compound (B1) or the compound (B2), and the compound (A1) or the compound (A2) can be obtained. The reaction temperature is not particularly limited, and may be, for example, 40 to 120° C. or the like. In addition, the reaction time is appropriately adjusted according to the amount of the compound and the like, and may be, for example, 1 to 40 hours.

Specific examples of the compound (B1) and the compound (B2) include the following compounds.

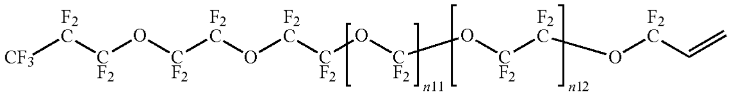
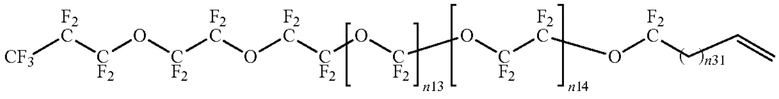
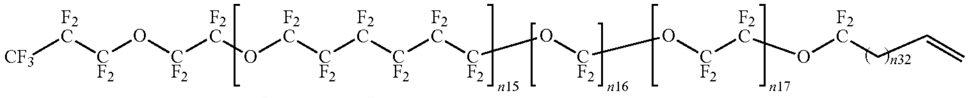
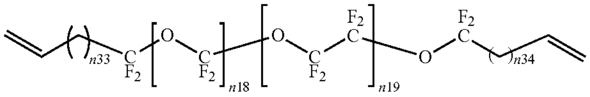
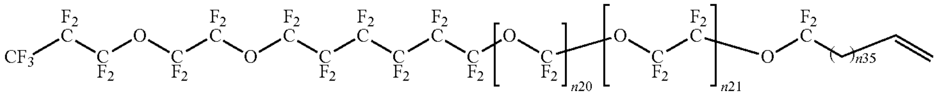
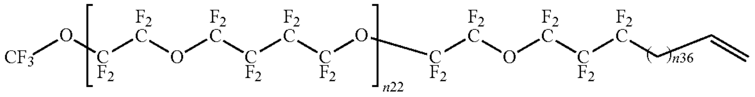
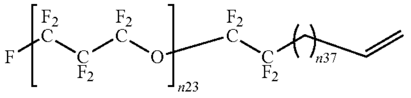
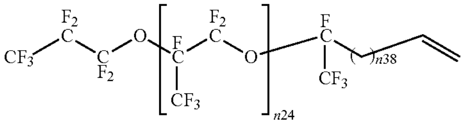

where n11 to n24 represent the number of repeating units and are each independently an integer of 1 to 200, n31 is an integer of 1 to 18, and n32 to n38 are each independently an integer of 0 to 18.

The compound (B1) and the compound (B2) can be obtained, for example, by an elimination reaction of a compound represented by the following formula (H1) or (H2).

$G^1$-X Formula (H1)

X-$G^2$-X Formula (H2)

where in the formula, $G^1$ and $G^2$ are as described above, and

X is a halogen atom.

[Method for Producing Compound (E1) or Compound (E2)]

In the method for producing a compound represented by the following formula (E1) or (E2) according to the present invention, the compound (A1) or the compound (A2) is reacted with a compound represented by the following formula (D).

$R^{11}—X^1$ Formula (D)

$G^1\text{-}(CH_2)_n—R^{11}$ Formula (E1)

$R^{11}—(CH_2)_n\text{-}G^2\text{-}(CH_2)_n—R^{11}$ Formula (E2)

where, in the formula, $G^1$, $G^2$, and n are as described above, and preferred embodiments are also the same, $R^{11}$ is a hydrocarbon group which may have a substituent or a heteroatom, and $X^1$ is a halogen atom.

Examples of the hydrocarbon group in $R^{11}$ include an aliphatic hydrocarbon group (linear alkyl group, branched alkyl group, cycloalkyl group, and the like), an aromatic hydrocarbon group (phenyl group and the like), and a group consisting of combinations thereof. The aliphatic hydrocarbon group may have a double bond or a triple bond in the carbon chain. Examples of the combination include a group in which an alkylene group and an aryl group are directly linked via a heteroatom.

Examples of the substituent that the hydrocarbon group may have include a halogen atom, a hydroxy group, an amino group, a nitro group, a sulfo group, and an oxo group, from the viewpoint of the stability of the compound in the present production method, a halogen atom is preferable. Examples of the halogen atom include a fluorine atom, a chlorine atom, and a bromine atom.

Heteroatoms may be included in the carbon chain alone or in combination with other substituents such as an oxo group. Specific examples of the partial structure containing the heteroatom include —C(O)$NR^{26}$—, —C(O)O—, —C(O)—, —O—, —$NR^{26}$—, —S—, —OC(O)O—, —NHC(O)O—, —NHC(O)$NR^{26}$—, —$SO_2NR^{26}$—, —$Si(R^{26})_2$—, —$OSi(R^{26})_2$—, —$Si(CH_3)_2$-Ph-$Si(CH_3)_2$—, and a divalent organopolysiloxane residue. Here, $R^{26}$ is a hydrogen atom, an alkyl group having 1 to 6 carbon atoms, or a phenyl group, and Ph is a phenylene group. From the viewpoint of ease of production of the present compound, the number of carbon atoms in the alkyl group of $R^{26}$ is preferably 1 to 3, and particularly preferably 1 and 2.

When another substituent is further introduced into the compound (E1) or the compound (E2), the hydrocarbon group in $R^{11}$ preferably has a carbon-carbon double bond. When the compound (E1) or the compound (E2) has a double bond, another substituent can be easily introduced by an addition reaction.

From the viewpoint of reactivity, the halogen atom in $X^1$ is preferably a chlorine atom, a bromine atom, or an iodine atom, more preferably a chlorine atom or a bromine atom, and still more preferably a bromine atom.

Preferred specific examples of the compound (D) include the following compounds.

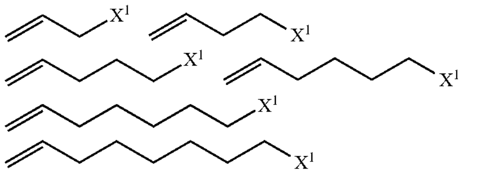

-continued

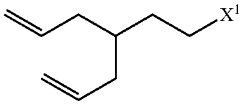

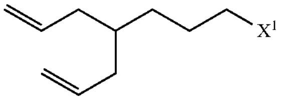

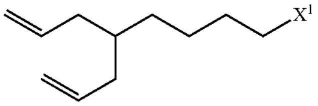

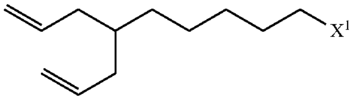

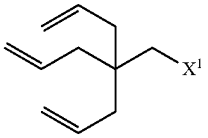

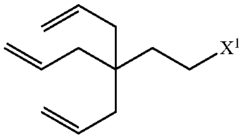

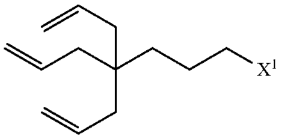

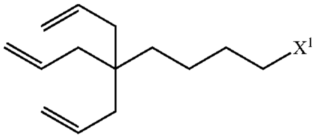

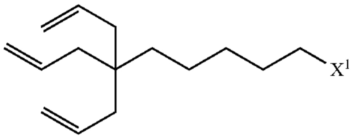

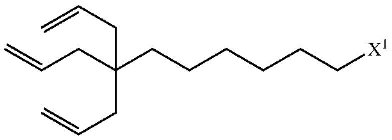

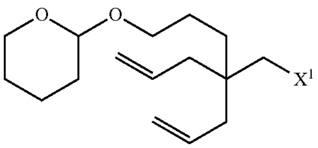

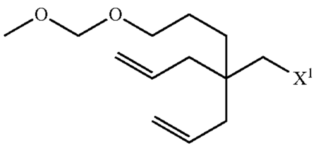

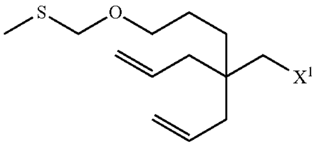

-continued

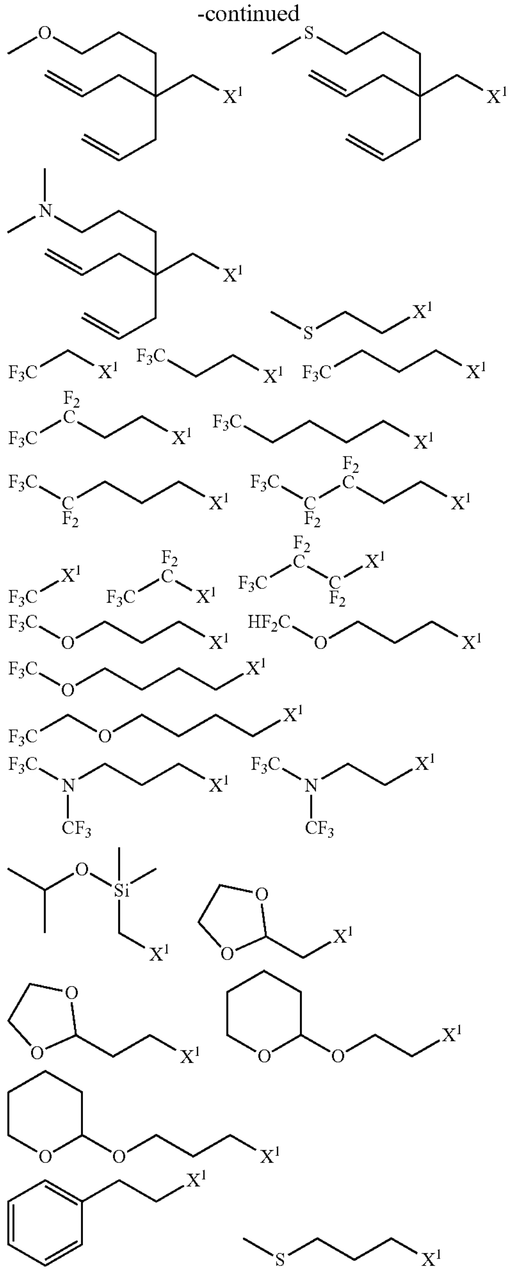

The compound (A1) or the compound (A2) and the compound represented by the following formula (D) can be reacted, for example, by heating in a solvent in the presence of a catalyst and a base.

Examples of the catalyst include known metal catalysts, and among them, transition metal compounds are preferable, and among them, compounds containing elements from groups 8 to 11 are more preferable, and compounds containing one or more elements selected from copper, nickel, palladium, and cobalt are preferable.

In the metal catalyst containing copper, the copper may be any of zerovalent, monovalent, divalent, and trivalent, and among them, monovalent or divalent copper salts or complex salts are preferable from the viewpoint of catalytic ability. Further, copper chloride is more preferable from the viewpoint of easy availability and the like. As copper chloride, either CuCl or $CuCl_2$ can be suitably used. In addition, copper chloride may be an anhydride or a hydrate, but copper chloride anhydride is more preferable from the viewpoint of catalytic ability.

In the metal catalyst containing nickel, the nickel may be any of zerovalent, monovalent, divalent, and trivalent, and among them, monovalent or divalent nickel salts or complex salts are preferable from the viewpoint of catalytic ability. Further, nickel chloride ($NiCl_2$) or nickel bromide (NiBr2) is more preferable from the viewpoint of easy availability and the like. In addition, nickel chloride may be an anhydride or a hydrate, but nickel chloride anhydride is more preferable from the viewpoint of catalytic ability. In addition, the nickel bromide may form a complex, and examples thereof include a nickel(II) bromide 2-methoxyethyl ether complex and a nickel(II) bromide ethylene glycol dimethyl ether complex.

In the metal catalyst containing palladium, the palladium may be any of a zerovalent compound, a monovalent compound, a divalent compound, and a trivalent compound, and among them, zerovalent or divalent palladium salts or complex salts are preferable from the viewpoint of catalytic ability. Furthermore, tris(dibenzylideneacetone)dipalladium ($Pd_2(dba)_3$) and palladium acetate ($Pd(OAc)_2$) are more preferable from the viewpoint of easy availability and the like. In addition, tris(dibenzylideneacetone)dipalladium and palladium acetate may be anhydrides or hydrates, but tris(dibenzylideneacetone)dipalladium anhydride and palladium acetate anhydride are more preferable from the viewpoint of catalytic ability.

In the reaction of the present production method, examples of the above ligand that may be used in combination with the metal catalyst as necessary include 1,3-butadiene, tricyclohexylphosphine, 1,1-bis(diphenylphosphino)ferrocene phenylpropyne, and tetramethylethylenediamine (TMEDA).

The base is preferably a strong base having low nucleophilicity, and examples thereof include potassium tert-butoxide, lithium diisopropylamide, potassium hexamethyldisilazide, and lithium-2,2,6,6-tetramethylpiperide.

In addition, the solvent may be appropriately selected from solvents inert to the present reaction. Examples thereof include ether-based solvents such as diethyl ether, tetrahydrofuran (THF), and dioxane. In addition, when the compound (A1) and the compound (A2) are compounds having a relatively high fluorine atom content, the fluorine-based solvent is preferably used alone or in combination with the solvent.

Examples of the fluorine-based solvent include hydrofluorocarbons (1H,4H-perfluorobutane, 1H-perfluorohexane, 1,1,1,3,3-pentafluorobutane, 1,1,2,2,3,3,4-heptafluorocyclopentane, 2H,3H-perfluoropentane, and the like), hydrochlorofluorocarbons (3,3-dichloro-1,1,1,2,2-pentafluoropropane, 1,3-dichloro-1,1,2,2,3-pentafluoropropane (HCFC-225cb), and the like), hydrofluoroethers ($CF_3CH_2OCF_2CF_2H$(AE-3000), (perfluorobutoxy)methane, (perfluorobutoxy)ethane, and the like), hydrochlorofluoroolefins ((Z)-1-chloro-2,3,3,4,4,5,5-heptafluoro-1-pentene (HCFO-1437 dycc (Z) form), (E)-1-chloro-2,3,3,4,4,5,5-heptafluoro-1-pentene (HCFO-1437 dycc (E) form), (Z)-1-chloro-2,3,3-trifluoro-1-propene (HCFO-1233 yd (Z) form), (E)-1-chloro-2,3,3-trifluoro-1-propene (HCFO-1233 yd (E) form), and the like), and fluorine-containing aromatic compounds (perfluorobenzene, m-bis(trifluoromethyl)benzene (SR-solvent), p-bis(trifluoromethyl)benzene, and the like).

[Method for Producing Surface Treatment Agent]

In the method for producing a surface treatment agent according to the present invention, a reactive silyl group is introduced into the compound (E1) or the compound (E2)

obtained by the above-described production method. The compound having a (poly)oxyfluoroalkylene chain and a hydrolyzable silyl group can form a surface layer exhibiting high lubricity, water/oil repellency, and the like on the surface of the substrate, and thus is suitably used as a surface treatment agent.

The method for introducing a reactive silyl group into the compound (E1) or the compound (E2) may be appropriately selected according to the substituent of the compound (E1) or the compound (E2). As an example, when the compound (E1) or the compound (E2) has a double bond, the compound (E1) or the compound (E2) can be introduced by subjecting the double bond and the following compound (J1) or (J2) to a hydrosilylation reaction.

$HSi(R^{40})_{3-c}(L)_c$ Formula (J1)

$HSi(R^{41})_{3-k}[—(OSi(R^{42})_2)_p—O—Si(R^{40})_{3-c}(L)_c]_k$ Formula (J2)

where, in the formula, $R^{40}$ is an alkyl group, and when there are a plurality of $R^{40}$'s, the $R^{40}$'s may be the same as or different from each other, L is a hydrolyzable group or a hydroxyl group, and a plurality of L's may be the same as or different from each other, $R^{41}$ is an alkyl group, and when there are a plurality of $R^{41}$'s, the $R^{41}$'s may be the same as or different from each other, $R^{42}$ is an alkyl group, a phenyl group, or an alkoxy group, and two $R^{42}$'s may be the same or different;

c is 2 or 3, k is 2 or 3, and p is an integer of 0 to 5, and when p is two or more, two or more $(OSi(R^{42})_2)$'s may be the same as or different from each other.

In addition, the compound (J1) may be synthesized, or a commercially available product may be used. In addition, the compound (J2) can be produced, for example, by the method described in International Patent Publication No. WO 2019/208503.

The reactive silyl group is a group in which one or both of a hydrolyzable group and a hydroxyl group are bonded to a silicon atom. The hydrolyzable group is a group that becomes a hydroxyl group by a hydrolysis reaction. That is, the hydrolyzable silyl group becomes a silanol group (Si—OH) by a hydrolysis reaction.

The silanol group further undergoes a dehydration condensation reaction between molecules to form a Si—O—Si bond. In addition, the silanol group undergoes a dehydration condensation reaction with a hydroxyl group (substrate —OH) on the surface of the substrate to form a chemical bond (substrate —O—Si).

Examples of the hydrolyzable group include an alkoxy group, a halogen atom, an acyl group, and an isocyanate group. The alkoxy group is preferably an alkoxy group having 1 to 6 carbon atoms.

The halogen atom is preferably a chlorine atom.

The hydrolyzable group is preferably an alkoxy group or a halogen atom from the viewpoint of ease of production. As the hydrolyzable group, an alkoxy group having 1 to 4 carbon atoms is preferable from the viewpoint of having less outgassing at the time of coating and being excellent in storage stability of the present compound, an ethoxy group is particularly preferable when long-term storage stability of the present compound is required, and a methoxy group is particularly preferable when the reaction time after coating the substrate with the surface treatment agent is shortened.

According to the above production method, for example, a surface treatment agent represented by the following formula is obtained.

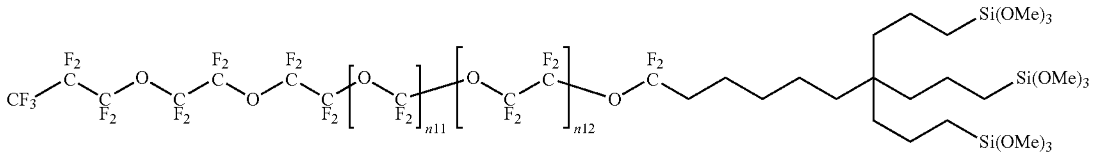

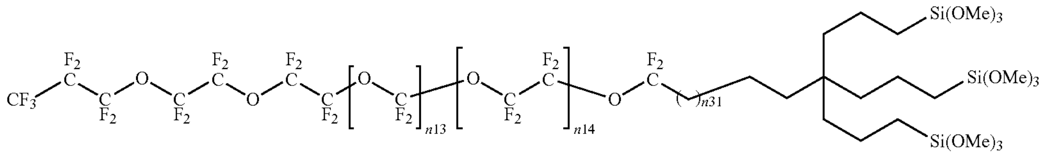

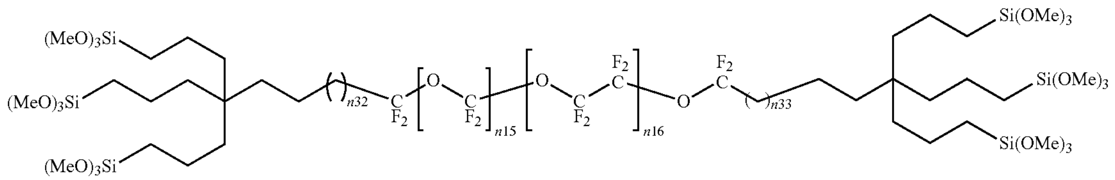

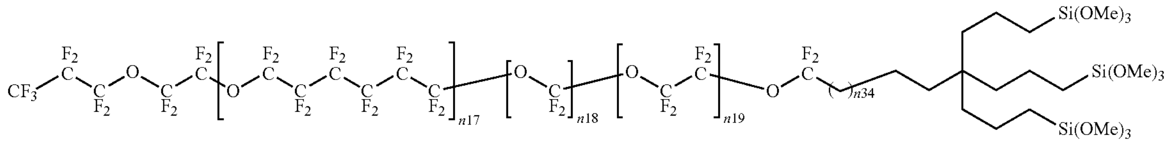

-continued

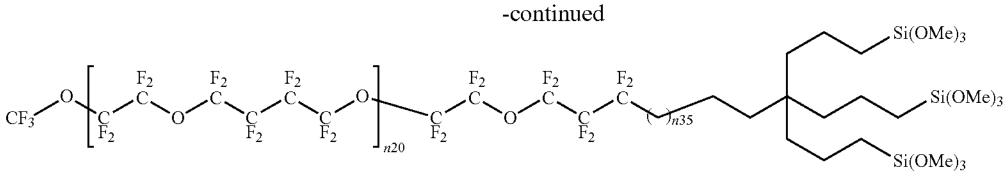

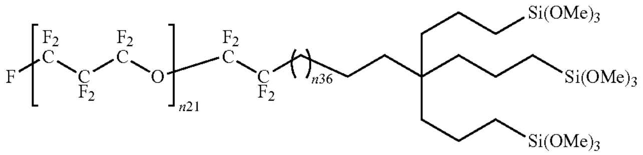

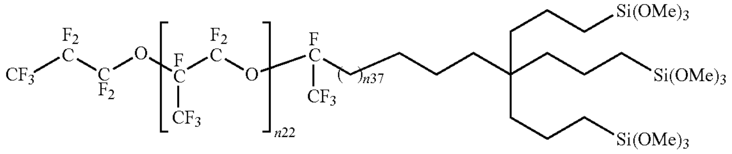

where n11 to n22 represent the number of repeating units and are each independently an integer of 1 to 200, and n31 to n37 are each independently an integer of 0 to 18.

Examples of the substrate to which the surface treatment agent is applied include substrates required to be imparted with water/oil repellency. Examples thereof include other articles (for example, stylus), substrates that may be used by being brought into contact with human fingers, substrates that may be held by human fingers during operation, and substrates that may be placed on other articles (for example, placing tables).

Examples of the material of the substrate include metal, resin, glass, sapphire, ceramic, stone, and composite materials thereof. The glass may be chemically strengthened. A base film such as a $SiO_2$ film may be formed on the surface of the substrate.

As the substrate, a substrate for a touch panel, a substrate for a display, and a spectacle lens are preferred, and a substrate for a touch panel is particularly preferred. The material of the substrate for a touch panel is preferably glass or a transparent resin.

In addition, as the substrate, glass or a resin film used for an exterior part (excluding a display unit) in a device such as a mobile phone (for example, a smartphone), a portable information terminal (for example, a tablet terminal), a game machine, or a remote controller is also preferable.

The surface treatment agents containing the fluorine-containing compound are suitably used for applications in which it is required to maintain performance (friction resistance) in which water/oil repellency is less likely to decrease even when the surface layer is repeatedly rubbed with a finger and performance (fingerprint dirt removability) in which a fingerprint attached to the surface layer can be easily removed by wiping, for a long period of time, for example, as a surface treatment agent for a member constituting a surface touched by a finger of a touch panel, a spectacle lens, and a display of a wearable terminal.

EXAMPLES

Hereinafter, the present invention will be described in detail using examples, but the present invention is not limited to these examples. In addition, Examples 1-2, 1-3, 2-4, 2-5, and 2-6 are examples of the production method.

Example 1

Example 1-1

In a 300 mL recovery flask, 44 g of allyltributyltin, 84 g of dodecane, and 7.8 g of tetrakis(triphenylphosphine)palladium were added, and the mixture was stirred and mixed at room temperature. Then, 51 g of the compound 1-1 was slowly added, and the mixture was stirred at 40° C. for 20 hours. The obtained crude liquid was filtered and then purified by distillation to obtain 33 g of the compound 1-2.

Compound 1-1

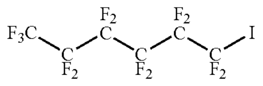

Compound 1-2

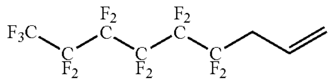

Example 1-2

In a 200 mL recovery flask, 15 g of the compound 1-2 and 100 g of a 0.5 M THF solution of 9-hydro-9-borabicyclo[2,2,0]nonane were added, and the mixture was stirred at 60° C. for 15 hours. The obtained crude liquid was purified by distillation to obtain 14 g of the compound 1-3.

Compound 1-3

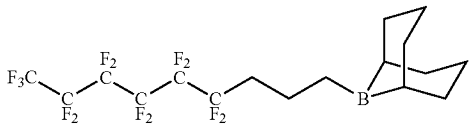

Example 1-3

In a 50 mL recovery flask, 1.5 g of the compound 1-3, 1.2 g of (2-bromoethyl)benzene, 10 g of tetrahydrofuran, 0.6 g of nickel(II) bromide 2-methoxyethyl ether complex, 0.33 g of trans-N,N'-dimethylcyclohexane-1,2-diamine, 0.55 g of t-butoxypotassium, and 0.73 g of isobutyl alcohol were added, and the mixture was stirred at 60° C. for 24 hours. Thereafter, hydrochloric acid was added, the mixture was extracted with ethyl acetate, and the organic layer was washed with a saturated sodium bicarbonate aqueous solution. The obtained organic layer was concentrated and then purified by silica gel column chromatography to obtain 0.9 g of the compound 1-4. In the following formula, R is $CH_2CH_2Phe$, and Phe is a phenyl group.

Compound 1-4

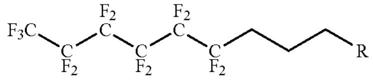

Example 2

Example 2-1

The following compound 2-1 was obtained according to the method described in Examples 11-1 to 11-3 of International Patent Publication No. WO 2013/121984.

$CF_3$—O—$(CF_2CF_2O$—$CF_2CF_2CF_2CF_2O)_nCF_2CF_2O$—$CF_2CF_2CF_2$—$CF_2OC(O)CF(CF_3)OCF_2CF_2CF_3$ Formula 2-1

Average value of the number of units n: 13

Example 2-2

In a 500 mL recovery flask shielded from light with aluminum foil, 5.8 g of sodium pyrithione and 100 mL of 1,3-bistrifluoromethylbenzene(trade name: SR-solvent) were input, and the mixture was stirred under ice cooling. Then, 50.0 g of the compound 2-1 was slowly input, and the mixture was stirred for 2 hours while being ice-cooled. Next, 12.0 g of iodine and 1.8 g of 2,2-azobis(2-methylbutyronitrile) (trade name: V-59) were input, the aluminum foil shielded from light was removed, and the mixture was stirred at 85° C. overnight. The temperature was returned to 25° C., methanol was input, and the mixture was sufficiently stirred. Thereafter, AC-6000 was input to separate two layers, and the lower layer was collected and distilled. The obtained crude product was purified by silica gel column chromatography to obtain 39.8 g of the following compound 2-2.

Compound 2-2

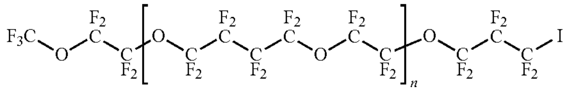

Average value of the number of units n: 13

Example 2-3

In a 300 mL recovery flask, 47 g of the compound 2-2, 20 g of allyltributyltin, 60 g of 1,3-bis(trifluoromethyl)benzene, and 0.32 g of 2,2'-azobis(2-methylbutyronitrile) were added, and the mixture was stirred at 90° C. for 24 hours. The obtained crude liquid was concentrated, then washed with hexane, and then purified by silica gel chromatography to obtain 42 g of the compound 2-3.

Compound 2-3

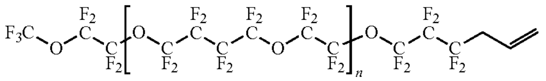

Example 2-4

In a 100 mL recovery flask, 10 g of the compound 2-3, 60 g of 1,3 bis(trifluoromethyl)benzene, and 8.3 g of a 0.5MTHF solution of 9-hydro-9-borabicyclo[2,2,0]nonane were added, and the mixture was stirred at 60° C. for 24 hours. The obtained crude liquid was concentrated to obtain 11 g of the compound 2-4.

Compound 2-4

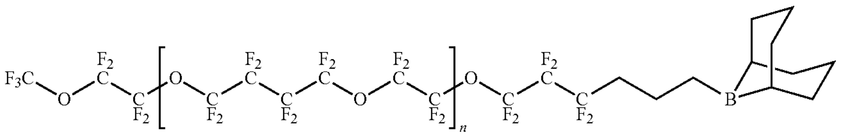

Example 2-5

In a 100 mL recovery flask, 11 g of the compound 2-4, 0.61 g of 6-bromo-1-hexene, 40 g of 1,3-bis(trifluoromethyl)benzene, 20 g of tetrahydrofuran, 0.5 g of nickel(II) bromide 2-methoxyethyl ether complex, 0.28 g of trans-N,N'-dimethylcyclohexane-1,2-diamine, 0.51 g of t-butoxypotassium, and 0.69 g of isobutyl alcohol were added, and the mixture was stirred at 60° C. for 24 hours. Thereafter, hydrochloric acid was added, the mixture was extracted with 1,3-bis(trifluoromethyl)benzene, and the organic layer was washed with a saturated sodium bicarbonate aqueous solution. The obtained organic layer was concentrated and then purified by silica gel column chromatography to obtain 5.1 g of the compound 2-5. R in the following formula is $CH_2CH_2CH_2CH_2CH{=}CH_2$.

Compound 2-5

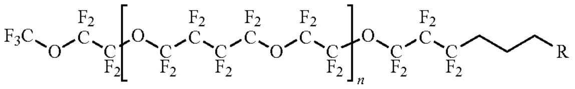

Example 2-6

In a 100 mL recovery flask, 10 g of the compound 2-3, 60 g of 1,3-bis(trifluoromethyl)benzene, and 0.26 g of 4,4,5,5-tetramethyl-1,3,2-dioxaborolane were added, and the mixture was stirred at 60° C. for 30 hours. The obtained crude liquid was concentrated and then purified by column chromatography to obtain 7 g of the compound 2-6.

Compound 2-6

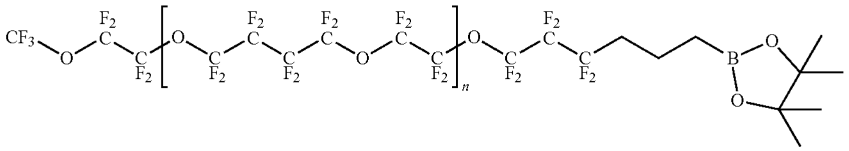

According to the present production method, any substituent can be introduced into a compound having a fluoroalkylene chain or a (poly)oxyfluoroalkylene chain under relatively mild reaction conditions using an easily available compound. The compound obtained by the present production method can be suitably used as, for example, a surface treatment agent capable of forming a surface layer having water/oil repellency, fingerprint wipe-off removability, and the like on a surface of a substrate, or a raw material thereof.

From the disclosure thus described, it will be obvious that the embodiments of the disclosure may be varied in many ways. Such variations are not to be regarded as a departure from the spirit and scope of the disclosure, and all such modifications as would be obvious to one skilled in the art are intended for inclusion within the scope of the following claims

What is claimed is:

1. A compound represented by the following formula (A1) or (A2):

$G^1\text{-}(CH_2)_n\text{-}M$ Formula (A1)

$M\text{-}(CH_2)_n\text{-}G^2\text{-}(CH_2)_n\text{-}M$ Formula (A2)

where, in the formula, $G^1$ is a monovalent group having a (poly)oxyfluoroalkylene chain, $G^2$ is a divalent group having a (poly)oxyfluoroalkylene chain, M is $BR^1R^2$, $R^1$ and $R^2$ are each independently a group represented by —OH, —$R^5$, —$OR^5$, —O—C(O)—$R^5$, or —$NR^5R^6$, $R^5$ is a hydrocarbon group which may have a substituent or a heteroatom in a carbon chain, two $R^5$'s may be linked to form a ring structure, $R^6$ is a hydrogen atom or an alkyl group having 1 to 6 carbon atoms, and when there are a plurality of M's, the M's may be the same as or different from each other, and n is an integer of 2 to 20.

2. A method for producing the compound according to claim 1, the method comprising: reacting a compound represented by the following formula (B1) or (B2) and a compound represented by the following formula (C1):

$G^1\text{-}(CH_2)_{n-2}—CH{=}CH_2$ Formula (B1)

$CH_2{=}CH—(CH_2)_{n-2}\text{-}G^2\text{-}(CH_2)_{n-2}—CH{=}CH_2$ Formula (B2)

$HBR^1R^2$ Formula (C1)

where, in the formula, $G^1$ is a monovalent group having a (poly)oxyfluoroalkylene chain, $G^2$ is a divalent group having a (poly)oxyfluoroalkylene chain, $R^1$ and $R^2$ are each independently a group represented by —OH, —$R^5$, —$OR^5$, —O—C(O)—$R^5$, or —$NR^5R^6$, $R^5$ is a hydrocarbon group which may have a substituent or a heteroatom in a carbon chain, two $R^5$'s may be linked to form a ring structure, and $R^6$ is a hydrogen atom or an alkyl group having 1 to 6 carbon atoms, and n is an integer of 2 to 20.

3. A method for producing a compound represented by the following formula (E1) or (E2), the method comprising: reacting the compound according to claim 1 with a compound represented by the following formula (D):

$R^{11}—X^1$ Formula (D)

$G^1\text{-}(CH_2)_n—R^{11}$ Formula (E1)

$R^{11}—(CH_2)_n\text{-}G^2\text{-}(CH_2)_n—R^{11}$ Formula (E2)

where, in the formula, $G^1$ is a monovalent group having a (poly)oxyfluoroalkylene chain, $G^2$ is a divalent group having a (poly)oxyfluoroalkylene chain, n is an integer of 2 to 20, $R^{11}$ is a hydrocarbon group which may have a substituent or a heteroatom, and $X^1$ is a halogen atom.

4. A method for producing a surface treatment agent, the method comprising: obtaining a compound represented by the formula (E1) or (E2) by the production method according to claim 3; and introducing a reactive silyl group into the compound.

5. The compound according to claim 1, wherein the compound is represented by the formula (A1).

6. The compound according to claim 1, wherein the compound is represented by the formula (A2).

7. The method according to claim 2, comprising: reacting the compound represented by the formula (B1) and the compound represented by the formula (C1).

8. The method according to claim 2, comprising: reacting the compound represented by the formula (B2) and the compound represented by the formula (C1).

9. The method according to claim 3, wherein the method produces the compound represented by formula (E1).

10. The method according to claim 3, wherein the method produces the compound represented by formula (E2).

* * * * *